United States Patent
Kim et al.

(10) Patent No.: US 11,504,328 B2
(45) Date of Patent: Nov. 22, 2022

(54) METHOD FOR PREPARING LIPOSOME COMPRISING ULTRASOUND REACTIVE MICROBUBBLE FOR DRUG DELIVERY AND LIPOSOME USING SAME

(71) Applicants: BIOINFRA LIFE SCIENCE INC., Seoul (KR); PACIFIC SYSTEM CO., LTD., Incheon (KR)

(72) Inventors: Chui Woo Kim, Seoul (KR); Dong Hee Park, Seoul (KR); Jong Ho Won, Seoul (KR)

(73) Assignees: BIOINFRA LIFE SCIENCE INC., Seoul (KR); PACIFIC SYSTEM CO., LTD., Incheon (KR)

( * ) Notice: Subject to any disclaimer, the term of this patent is extended or adjusted under 35 U.S.C. 154(b) by 83 days.

(21) Appl. No.: 16/982,485

(22) PCT Filed: Mar. 20, 2019

(86) PCT No.: PCT/KR2019/003248
§ 371 (c)(1),
(2) Date: Sep. 18, 2020

(87) PCT Pub. No.: WO2019/182353
PCT Pub. Date: Sep. 26, 2019

(65) Prior Publication Data
US 2021/0015751 A1  Jan. 21, 2021

(30) Foreign Application Priority Data

Mar. 20, 2018 (KR) .................. 10-2018-0032206
Mar. 20, 2019 (KR) .................. 10-2019-0031738

(51) Int. Cl.
*A61K 9/127* (2006.01)
*A61K 41/00* (2020.01)
(Continued)

(52) U.S. Cl.
CPC ........ *A61K 9/1277* (2013.01); *A61K 41/0047* (2013.01); *A61K 47/10* (2013.01);
(Continued)

(58) Field of Classification Search
CPC ............................. A61K 9/1277; A61K 9/127
See application file for complete search history.

(56) References Cited

U.S. PATENT DOCUMENTS 5,088,499 A * 2/1992 Unger .................. A61K 49/227
424/44
5,215,680 A * 6/1993 D'Arrigo ........... A61K 49/1815
424/9.34
(Continued)

FOREIGN PATENT DOCUMENTS

CN    105727320 A    7/2016
CN    106102720 A    11/2016
(Continued)

OTHER PUBLICATIONS

Shirshendu Paul, Rahul Nahire, Sanku Mallik, Kausik Sarkar. "Encapsulated microbubbles and echogenic liposomes for contrast ultrasound imaging and targeted drug delivery." Computational Mechanics, vol. 53, 2014, pp. 413-435. (Year: 2014).*
(Continued)

*Primary Examiner* — Isaac Shomer
(74) *Attorney, Agent, or Firm* — Holzer Patel Drennan

(57) ABSTRACT

Provided are a method for preparing liposomes comprising ultrasound reactive microbubbles for drug delivery, comprising (a) a step of producing ultrasound reactive microbubbles comprising an inert gas therein and having a first shell formed on the outer surface thereof, followed by forming a uniform size distribution of the ultrasound reactive microbubbles through an extruder; and (b) a step of producing liposomes comprising the ultrasound reactive
(Continued)

microbubbles distributed in a uniform size and a medicament therein and having a second shell formed on the outer surface thereof, followed by forming a uniform size distribution of the liposomes through an extruder; and a liposome using same.

24 Claims, 11 Drawing Sheets

(51) Int. Cl.
    *B01F 23/80*     (2022.01)
    *B01F 23/41*     (2022.01)
    *B01F 101/22*     (2022.01)
    *A61K 47/42*     (2017.01)
    *A61K 47/10*     (2017.01)

(52) U.S. Cl.
    CPC .......... *A61K 47/42* (2013.01); *B01F 23/4105* (2022.01); *B01F 23/808* (2022.01); *B01F 23/4143* (2022.01); *B01F 2101/22* (2022.01)

(56) References Cited

U.S. PATENT DOCUMENTS

| | | | | |
|---|---|---|---|---|
| 2008/0095716 | A1* | 4/2008 | Tessari | A61K 9/122 424/9.52 |
| 2009/0220584 | A1* | 9/2009 | Goodwin | A61P 35/00 435/375 |
| 2012/0109045 | A1 | 5/2012 | Wrenn et al. | |
| 2014/0134234 | A1* | 5/2014 | Grayburn | A61K 9/127 424/450 |
| 2016/0250252 | A1* | 9/2016 | Holland | A61K 41/0028 424/450 |
| 2016/0375156 | A1* | 12/2016 | Seo | A61K 47/06 424/9.52 |

FOREIGN PATENT DOCUMENTS

| | | | |
|---|---|---|---|
| KR | 1020140018150 A | 2/2014 | |
| KR | 1020150105228 A | 9/2015 | |
| WO | WO-2014021678 A1 * | 2/2014 | ........... A61K 31/337 |

OTHER PUBLICATIONS

Ine Lentacker, Stefaan C. De Smedt, and Niek N. Sanders. "Drug loaded microbubble design for ultrasound triggered delivery." Soft Matter, vol. 5, 2009, pp. 2161-2170. (Year: 2009).*

Stuart Ibsen, Carolyn E Schutt, and Sadik Esener. "Microbubble-mediated ultrasound therapy: a review of its potential in cancer treatment." Drug Design, Development and Therapy, vol. 7, 2013, pp. 375-388. (Year: 2003).*

Delia Danila et al. "Antibody-Labeled Liposomes for CT Imaging of Atherosclerotic Plaques." Texas Heart Institute Journal, vol. 36(5), 2009, pp. 393-403. (Year: 2009).*

English Translation of WO2014021678A1. "Microbubble-nanoliposome complex for cancer diagnosis and treatment." Obtained from https://patents.google.com/patent/WO2014021678A1/en?q=microbubble+nanoliposome+complex&oq=microbubble+nanoliposome+complex on Apr. 22, 2022, originally published 2014, pp. 1-18 (Year: 2014).*

Stuart Ibsen et al. "A novel nested liposome drug delivery vehicle capable of ultrasound triggered release of its payload." Journal of Controlled Release, vol. 155, 2011, pp. 358-366. (Year: 2011).*

N. Berger et al. "Filter extrusion of liposomes using different devices: comparison of liposome size, encapsulation efficiency, and process characteristics." International Journal of Pharmaceutics, vol. 223, 2001, pp. 55-68. (Year: 2001).*

Kheirolomoom, A., et al. "Acoustically active microbubbles conjugated to liposomes: characterization of a proposed drug delivery vehicle," Journal of Controlled Release, 2007, vol. 118, No. 3, pp. 275-284.

Search report issued for International Application PCT/KR2019/003248 dated Jul. 4, 2019.

First Office Action issued by China National Intellectual Property Administration dated Apr. 29, 2022 for application No. 201980020482. 8, Reference is mostly in Chinese—only English text considered.

Fu, Ching-Kuo , et al., "Targeted Liposomes Antibody-Modified Liposomes", World Latest Medical Information Digest, Dec. 2003.

* cited by examiner (A) FLUORESCENCE MICROSCOPE IMAGE (B) OPTICAL MICROSCOPE IMAGE (C) MERGED IMAGE

FIG. 4B

DISTRIBUTION RESULTS (CONTIN)

| INTENSITY DISTRIBUTION | | VOLUME DISTRIBUTION | | | NUMBER DISTRIBUTION | | |
|---|---|---|---|---|---|---|---|
| PEAK | DIAMETER(nm) | STD. DEV. | PEAK | DIAMETER(nm) | STD. DEV. | PEAK | DIAMETER(nm) | STD. DEV. |
| 1 | 308.0 | 137.9 | 1 | 184.4 | 73.7 | 1 | 139.5 | 37.5 |
| 2 | 0.0 | 0.0 | 2 | 0.0 | 0.0 | 2 | 0.0 | 0.0 |
| 3 | 0.0 | 0.0 | 3 | 0.0 | 0.0 | 3 | 0.0 | 0.0 |
| 4 | 0.0 | 0.0 | 4 | 0.0 | 0.0 | 4 | 0.0 | 0.0 |
| 5 | 0.0 | 0.0 | 5 | 0.0 | 0.0 | 5 | 0.0 | 0.0 |
| AVERAGE | 308.0 | 137.9 | AVERAGE | 184.4 | 73.7 | AVERAGE | 139.5 | 37.5 |

FIG. 4C

| CUMULANTS RESULTS | | | |
|---|---|---|---|
| DIAMETER | (d) | :257.1 | (nm) |
| POLYDISPERSITY INDEX | (P.I.) | :0.145 | |
| DIFFUSION CONST | (D) | :1.913e-008 | (cm²/sec) |
| RESIDUAL | | :2.658e-003 | (O.K) |

| MEASUREMENT CONDITION | | |
|---|---|---|
| TEMPERATURE | : 25.0 | (°C) |
| DILUENT NAME | : WATER | |
| REFRACTIVE INDEX | : 1.3328 | |
| VISCOSITY | : 0.8878 | (cP) |
| SCATTERING INTENSITY | : 25762 | (cps) |
| ATTENUATOR 1 | : 0.72 | (%) |

METHOD FOR PREPARING LIPOSOME COMPRISING ULTRASOUND REACTIVE MICROBUBBLE FOR DRUG DELIVERY AND LIPOSOME USING SAME

FIELD OF THE DISCLOSURE

The present disclosure relates to a method for preparing liposomes for drug delivery containing drugs and microbubbles reactive to ultrasound and the liposomes using the same.

More particularly, the present disclosure relates to the method for preparing the liposomes for drug delivery containing the microbubbles reactive to the ultrasound, comprising steps of: (a) generating the microbubbles such that the microbubbles have first shells respectively as outer surfaces thereof and include inert gas inside the first shells and then adjusting sizes of the microbubbles to follow a first uniform distribution by using a first filter in an extruder; and (b) generating the liposomes such that the liposomes have second shells respectively as outer surfaces thereof and respectively include (1) the microbubbles whose sizes follow the first uniform distribution and (2) drugs, and then adjusting sizes of the liposomes to follow a second uniform distribution by using a second filter in the extruder, and the liposomes using the same.

BACKGROUND OF THE DISCLOSURE

A drug delivery system (DDS) is a dosage formulation for efficiently delivering drugs in the amount necessary for treatment of diseases, resulting in minimizing side effects of the drugs and optimizing therapeutic effects of the drugs.

Such a drug delivery system may be realized by using at least one of a transdermal, oral or vascular method, etc., depending on a route of administration. In addition, the drug delivery system that introduces micro-sized capsules into blood vessels to treat an affected area is in the spotlight as a treatment technology in the future.

Among the technologies of the drug delivery system, a technique for accurately targeting a drug to the affected area and a technique for controlling drug release in the affected area are considered as important technologies. Therefore, a targeted drug delivery system using ultrasound and microbubbles reactive to the ultrasound has recently attracted more attention as a solution to these problems.

In particular, according to research that ultrasonic energy generates cavitation and that the cavitation enhances the drug delivery into the skin or cells, in order to deliver the drugs to a human body, desired drugs or receptors are allowed to be combined with shells of the microbubbles, commonly used as an ultrasound contrast agent, through ligand binding.

However, the microbubbles cannot be a perfect drug carrier due to a limitation that the drugs are binded to outer surfaces of the shells which may cause loss of the drugs while the microbubbles are transported to a target site. Also, it has a limitation that the loaded amount of the drugs may not be sufficiently large.

In order to improve this, a technology for manufacturing liposomes into which the microbubbles and the drugs are simultaneously loaded to increase a reactivity to ultrasonic energy has emerged recently.

However, a method of simultaneously loading the drugs and the microbubbles containing inert gas into the shells of a liposome has a disadvantage that it is difficult to form a multi-layered structure and to load the drugs effectively thereinto.

That is, the loaded amount of the drugs may depend on sizes of the microbubbles and the characteristics of the drugs captured inside the liposomes, and in the worst case, the liposomes may fail to load the drugs or the microbubbles.

SUMMARY OF THE DISCLOSURE

It is an object of the present disclosure to solve all the aforementioned problems.

It is another object of the present disclosure to protect drugs from external environment by encapsulating the drugs into liposomes.

It is still another object of the present disclosure to prevent drug release into normal tissue and deliver the drugs only to a target site where ultrasound energy is to be irradiated, taking advantage of a high reactivity to the ultrasound energy.

It is still yet another object of the present disclosure to produce microbubbles whose sizes follow a first uniform distribution and the liposomes whose sizes follow a second uniform distribution, to thereby quantify an amount of the drugs to be loaded into the liposomes.

It is still yet another object of the present disclosure to allow the drugs to be loaded in an amount sufficient for an effective dose.

In order to accomplish objects above, representative structures of the present disclosure are described as follows.

In accordance with one aspect of the present disclosure, there is provided a method for preparing liposomes for drug delivery containing microbubbles reactive to ultrasound, including steps of: (a) generating the microbubbles such that the microbubbles have first shells respectively as outer surfaces thereof and include inert gas inside the first shells and then adjusting sizes of the microbubbles to follow a first uniform distribution by using an extruder including a first filter; and (b) generating the liposomes such that the liposomes have second shells respectively as outer surfaces thereof and respectively include (1) the microbubbles whose sizes follow the first uniform distribution and (2) drugs and then adjusting sizes of the liposomes to follow a second uniform distribution by using the extruder including a second filter.

In accordance with another aspect of the present disclosure, there is provided liposomes for drug delivery containing microbubbles reactive to ultrasound, including: the microbubbles generated to have first shells respectively as outer surfaces thereof and include inert gas inside the first shells and then to have sizes thereof adjusted and follow a first uniform distribution by using an extruder including a first filter; and the liposomes generated to have second shells respectively as outer surfaces thereof and respectively include (1) the microbubbles whose sizes follow the first uniform distribution and (2) drugs, and then to have sizes thereof adjusted and follow a second uniform distribution by using the extruder including a second filter.

BRIEF DESCRIPTION OF THE DRAWINGS

The above and other objects and features of the present disclosure will become apparent from the following description of preferred embodiments given in conjunction with the accompanying drawings, in which:

FIGS. 4A to 4C are drawings schematically illustrating results of analyzing granularity of the microbubbles, the results showing an intensity distribution, a volume distribution, and a number distribution in accordance with one example embodiment of the present disclosure.

DETAILED DESCRIPTION OF THE PREFERRED EMBODIMENTS

Figure 1:
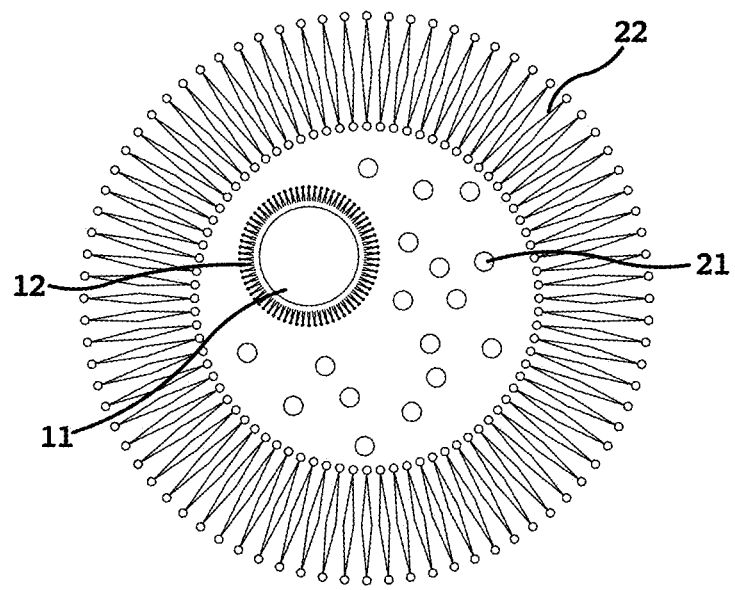
FIG. 1 is a drawing schematically illustrating one of liposomes for drug delivery containing drugs and one of microbubbles reactive to ultrasound in accordance with one example embodiment of the present disclosure.

In the following detailed description, reference is made to the accompanying drawings that show, by way of illustration, specific embodiments in which the present disclosure may be practiced. These embodiments are described in sufficient detail to enable those skilled in the art to practice the present disclosure. It is to be understood that the various embodiments of the present disclosure, although different, are not necessarily mutually exclusive. For example, a particular feature, structure, or characteristic described herein in connection with one embodiment may be implemented within other embodiments without departing from the spirit and scope of the present disclosure. In addition, it is to be understood that the position or arrangement of individual elements within each disclosed embodiment may be modified without departing from the spirit and scope of the present disclosure. The following detailed description is, therefore, not to be taken in a limiting sense, and the scope of the present disclosure is defined only by the appended claims, appropriately interpreted, along with the full range of equivalents to which the claims are entitled. In the drawings, like numerals refer to the same or similar functionality throughout the several views. The headings and abstract of the present disclosure provided herein are for convenience only and do not limit or interpret the scope or meaning of the embodiments.

To allow those skilled in the art to carry out the present disclosure easily, the example embodiments of the present disclosure will be explained in detail by referring to attached diagrams as shown below.

FIG. 1 is a drawing schematically illustrating one of liposomes for drug delivery containing one of microbubbles 11 reactive to ultrasound in accordance with one example embodiment of the present disclosure. Herein, the liposomes may be double layered, and the microbubbles, e.g., a micelle, may be single layered.

By referring to FIG. 1, the microbubbles 11 may respectively have first shells 12 as outer surfaces thereof. And the liposomes for drug delivery may respectively have second shells 22 as outer surfaces thereof and may respectively have the microbubbles 11 therein. And, drugs 21 may be loaded into space between the first shells 12 and the second shells 22.

The liposomes as such may be produced by (i) creating the microbubbles 11 whose sizes follow a first uniform distribution by using a first filter in an extruder, (ii) creating the liposomes such that the liposomes respectively have the second shells 22 as outer surfaces thereof and respectively include (1) the drugs and (2) the microbubbles 11 whose sizes follow the first uniform distribution, and (iii) adjusting sizes of the liposomes to follow a second uniform distribution by using a second filter in the extruder in accordance with one example embodiment of the present disclosure.

Processes of creating the microbubbles 11 reactive to the ultrasound are described in detail below.

First, solution of source material for the first shells may be prepared.

The solution of the source material for the first shells may be prepared by dissolving first mixture powders, including first lipids, in first solvent. The first mixture powders including the first lipids may further have at least one of albumin, one or more polymers, PEG (polyethylene glycol), one or more surfactants, one or more proteins, and one or more biodegradable macromolecules, and may further have cholesterol in order to increase a durability of the microbubbles.

Also, the first lipids may include at least one of DPPC (1,2-Dipalmitoyl-sn-glycerol-3-phosphocholine), HSPC (phosphatidylcholine), DDPC(1,2-didecanoyl-sn-glycerol-3-phosphocholine), DEPC(1,2-Di(cis-13-docosenoyl)-sn-glycerol-3-phosphocholine), DOPC(1,2-Dioleoyl-sn-glycerol-3-phosphocholine), DMPC(1,2-Dimyristoyl-sn-glycerol-3-phosphorylcholine), DLPC(1,2-Dilauroyl-sn-glycerol-3-phosphorylcholine), DEPC(1,2-Didecanoyl-sn-glycerol-3-phosphocholine), DSPC(1,2-Distearoyl-sn-glycerol-3-phosphocholine), MPPC(1-myristoyl-2-palmitoyl-sn-glycerol-3-phosphocholine), MSPC(1-myristoyl-2-stearoyl-sn-glycerol-3-phosphocholine), egg PC(phosphocholine), DPPA(Diphenylphosphoryl azide), DMPA-Na(1,2-Dimyristoyl-sn-glycerol-3-phosphate), DPPA-Na(1,2-Dipalmitoyl-sn-glycerol-3-phosphate), DOPA-Na(1,2-Dioleoyl-sn-glycerol-3-phosphate), DSPE (Distearoylphosphatidylethanolamine), DMPE(Dimyristoyl phosphatidylethanolamine), DOPE(Dioleoyl phosphatidylethanolamine), DPPE(Dipalmitoyl phosphatidylethanolamine), DOPE-Glutaryl-(Na)2(1,2-Dioleoyl-sn-glycerol-3-phosphoethanolamine), egg PE(phosphatidylethanolamine), DSPG(Distearoyl phosphatidylglycerol), DMPG-Na(1,2-Dimyristoyl-sn-glycerol-3-Phosphoglycerol), DPPG-Na(1,2-Dipalmitoyl-sn-glycerol-3-Phosphoglycerol), DOPG-Na(1,2-Dioleoyl-sn-glycerol-3-Phosphoglycerol), DOPS (dioleoyl phosphatidylserine), DMPS(Dimyristoyl phosphatidylserine), DMPS-Na(1,2-Dimyristoyl-sn-glycerol-3-phosphoserine), DPPS-Na(1,2-Dipalmitoyl-sn-glycerol-3-phosphoserine), DOPS-Na(1,2-Dioleoyl-sn-glycerol-3-phosphoserine), DSPS (Distearoylphosphatidylserine), DSPE-mPEG(1,2-distearoyl-sn-glycerol-3-phosphoethanolamine-N-[methoxy (polyethylene glycol)-2000]), DSPE-mPEG-2000-Na(1,2-Distearoyl-sn-glycerol-3-phosphoethanolamine), DSPE-mPEG-5000-Na, DSPE-Maleimide PEG-2000-Na, Surfactant: Tween 80, Span 80, dipotassium glycyrrhizinate.

Also, the albumin may include serum albumin, ovalbumin, etc.

Also, the polymers may include poly(β-benzyl-L-aspartate), PDLA (poly-DL-lactic acid), etc.

Also, the surfactants may include sodium fatty acid, monoalkyl sulfate, alkylpolyoxyethylene sulfate, alkylbenzenesulfonate, monoalkyl phosphate, dialkyldimethylammonium salt, alkylbenzylmethylammonium salt, alkylsulfobetaine, alkylcarboxybetaine, polyoxyethylene alkyl ethers, fatty acid sorbitan esters, fatty acid diethanolamines, alkyl monoglyceryl ethers, benzalkonium chloride, benzethonium chloride, etc.

Also, the proteins may include the albumin, globulins, collagen, etc.

Also, the biodegradable macromolecules may include PHB-based plastics, polysaccharide-based plastics, polycaprolactone (PCL), polylactic acid (PLA), propylene glycolic acid (PG), polyhydroxybutyrate-co-valerate (PHBV), polyvinyl alcohol (PVA), polybutylene succinate, chitin-based plastics, oil-based plastics, etc.

Also, the first solvent may include at least one of (i) saline and/or triple distilled water, (ii) glycerin, and (iii) propylene glycol.

As one example, the solution of the source material for the first shells may be prepared by dissolving powder solutes such as lipids, the albumin, the polymers, the cholesterol, the PEG (polyethylene glycol), etc. to be used for the shells in solvent including at least one of the saline and/or the triple distilled water (40 to 60%), the glycerin (2 to 10%), and the propylene glycol (40 to 60%), at the temperature of 60° C. to 100° C. for one to six hours.

As one example, the microbubbles reactive to the ultrasound may be comprised mainly of the DPPC (dipalmitoyl-phosphatidyl-choline) and the DPPA (diphenyl-phosphoryl-azide) as shell material to capture inert gas and to increase a stability of the microbubbles. Herein, the normal saline, the glycerol, the propylene glycol may further be added as the shell material.

And, the cholesterol may further be added in order to increase a durability of the microbubbles when the DPPC and the DPPA form the shells.

Next, the solution of the source material for the first shells may be mixed with the inert gas in order to increase a reactivity to the ultrasound energy.

Herein, the inert gas may be perfluorocarbon-based gas which includes at least one of perfluoromethane, perfluoroethane, perfluoropropane, perfluorobutane, perfluoro-n-pentane, perfluoro-n-hexane, perfluoromethylcyclopentane, perfluoro-1,3-dimethylcyclohexane, perfluorodecalin, perfluoromethyldecalin, perfluoroperhydrobenzyltetralin, etc.

As one example, (1) the solution of the source material for the first shells and (2) the inert gas may be mixed by a volume ratio of 1:1 to 20:1, and may be dispensed in vials which are then sealed, and the solution and the inert gas in the vials may be mechanically blended by a vial mixer.

Herein, rotational speed of the mechanical blending may be set as 1,000 to 5,000 rpm so that the sizes and a granularity of the microbubbles 11 are appropriately adjusted.

Then, the perfluorocarbon-based inert gas may be broken down into nano-sized or micro-sized particles of an O/W type emulsion through the mechanical blending, and the inert gas may be combined with hydrophobic tails of amphipathic phospholipids through self-assembling, resulting in a stable state of the combined inert gas. And as a result, the microbubbles 11 having the inert gas therein may be formed as shown in FIG. 1.

Specifically, the phospholipids are amphipathic, that is, fatty acid chains corresponding to the tails of the phospholipids are hydrophobic, and phosphoric acid and bases corresponding to heads of the phospholipids are hydrophilic. The amphipathic phospholipids as such serve an important role in forming the shells. And, the microbubbles 11 may be reactive to the ultrasound.

Figure 2:
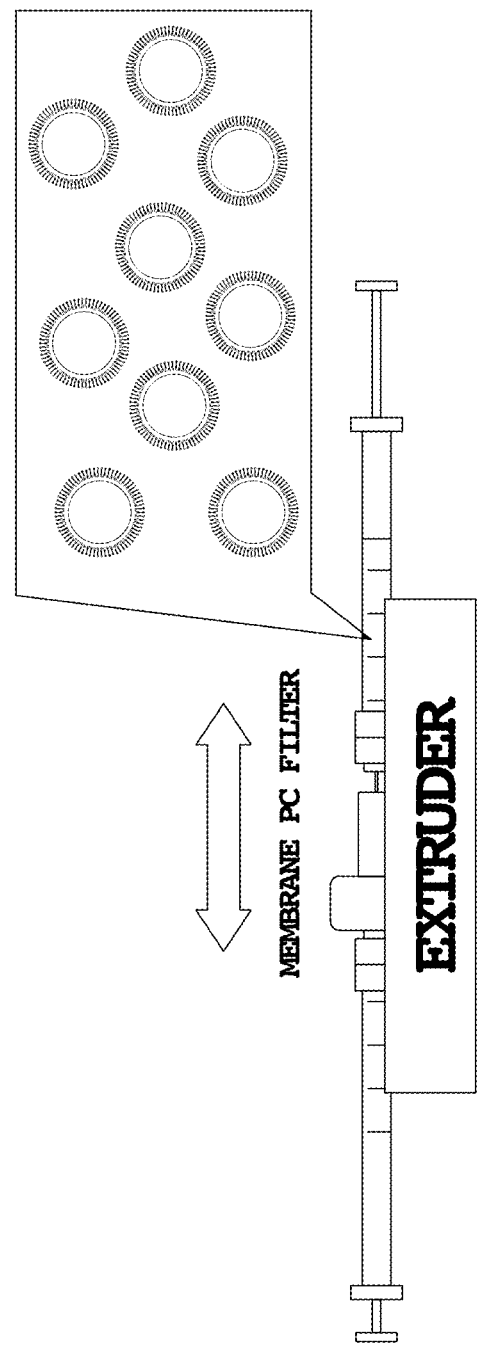
FIG. 2 is a drawing schematically illustrating a process of adjusting sizes of the microbubbles in accordance with one example embodiment of the present disclosure.

Next, as shown in FIG. 2, the microbubbles 11 with various sizes may be filtered by using the first filter with a first pore size ranging from 30 nm to 1 μm, to thereby adjust the sizes of the microbubbles 11 to follow the first uniform distribution. Herein, the first filter may be a membrane filter comprised of polycarbonates.

Also, temperature at which the microbubbles 11 are filtered may vary from room temperature to phase transition temperature of each material, and the filtering may be performed five times or more.

Thereafter, a mixture which includes the microbubbles 11 whose sizes follow the first uniform distribution through filtering is centrifuged, to thereby precipitate the microbubbles 11. Then supernatant liquid is removed, and remainings are washed with DW (deionized water), and accordingly, the microbubbles 11 adjusted to a first desired size may be acquired.

A first example embodiment: producing the microbubbles reactive to the ultrasound 1. Preparing Lipid Shell Material Lipid powders of the DPPC and the DPPA are put into solvent where the normal saline, the glycerol, and the propylene glycol are included, then solution is heated by a hot plate for 3 hours without boiling and overflowing. Herein, the saline, the glycerol, and the propylene glycol may be mixed by a volume ratio of 20:1:21 to generate the solvent, and the lipid powders of the DPPC (0.1 g) and the DPPA (0.01 g) may be dissolved into a total of 100 ml of the solvent to generate solution. Herein, the DSPE-mPEG (0.127 g) may further be added to the solvent. And microwaves may be used for heating the solution.

2. Preparing Cholesterol Shell Material

Solvent of a total of 100 ml of the normal saline and the propylene glycol (and the glycerol which may be omitted) may be put into a glass beaker. Then the cholesterol (0.127 g) may be put into the solvent to generate solution, and then the solution may be heated by the hot plate for 3 hours at a temperature of 80° C.

3. Producing the Microbubbles Reactive to the Ultrasound

The solution (0.5 ml) of the cholesterol is blended with the solution (1.5 ml) of the DPPC and the DPPA. And the perfluorocarbon-based gas is mixed with the blended solution of the cholesterol, the DPPC and the DPPA by a volume ratio of 1:20 and dispensed into a 2 ml vial which is then sealed. Next, the solution of the perfluorocarbon-based gas, the cholesterol, the DPPC and the DPPA is mechanically blended for 45 seconds. For example, the solution (0.5 ml) of the cholesterol is blended with the solution (1.5 ml) of the DPPC and the DPPA, and 2 ml of the solution of the cholesterol, the DPPC, the DPPA and 0.1 ml of perfluorobutane are mixed and dispensed into the 2 ml vial, then the vial is sealed and vibrated for 45 seconds. Herein, a frequency of the vibration may be set as 4,530±100 vibrations per minute.

That is, as one example of producing the microbubbles 11 in the first example embodiment, the DPPC (0.1 g), the DPPA (0.01 g), and the cholesterol (0.127 g) are dissolved in the solvent, and the amount of the inert gas is, in case of the perfluorobutane, 10 to 100 μl (equivalent to masses of 17.5 to 175 mg) at a liquid state (−80° C. to −20° C.)

4. Adjusting the Sizes of the Microbubbles and Separating the Microbubbles

First, the microbubbles 11 with various sizes are filtered by using the extruder including the polycarbonate membrane filter, and the filtered microbubbles 11 are centrifuged, to thereby precipitate the microbubbles 11. Then the supernatant liquid is removed and the remainings are washed with the DW (deionized water), and accordingly, the microbubbles 11 whose sizes follow the first uniform distribution may be acquired.

5. Analysis by Using a Confocal Microscope

Figure 3:
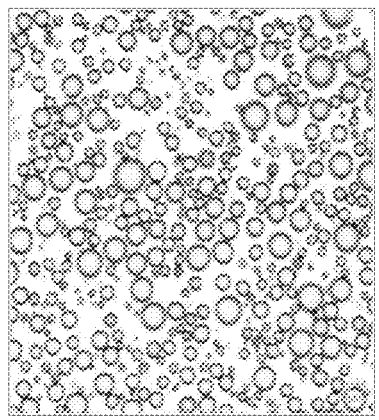
FIG. 3 is a drawing schematically illustrating confocal microscope images of the microbubbles in accordance with one example embodiment of the present disclosure.
Figure 3:
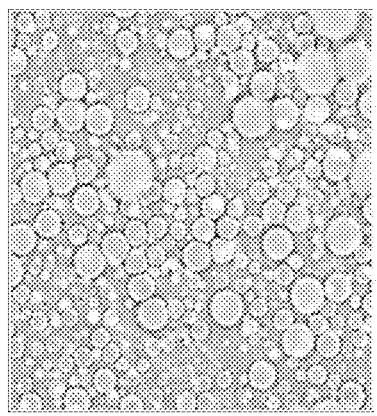
Figure 3:
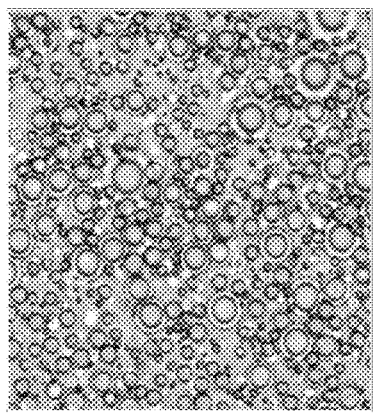

In order to confirm whether the microbubbles are formed, to analyze shapes of the microbubbles, and to identify correlation among the microbubbles and fluorescent lipids, confocal microscope images as shown in FIG. 3 are acquired of the microbubbles produced from NBD PC according to the method of the first example embodiment above.

In FIG. 3, (A) shows a fluorescence microscope image, (B) shows an optical microscope image, and (C) shows an image generated by merging the fluorescence microscope image and the optical microscope image.

As can be seen in (A) and (B) of FIG. 3, the fluorescent lipids form shell-like boundaries of the microbubbles, and core portions are empty or comprised of gas, not of the lipids.

And as can be seen in (C) of FIG. 3, common air bubbles and the microbubbles may be distinguished respectively as bubbles not comprised of the fluorescent lipids and bubbles comprised of the fluorescent lipids, and most of the shells are comprised of the fluorescent lipids.

6. Granularity Analysis

In the granularity analysis, sizes of particles are measured by using light of lasers diffracted or scattered from samples. Details of an apparatus used for the granularity analysis of the microbubbles are as follows.

A. Model: ELS-2000ZS
B. Granularity analysis: DLS (Dynamic Light Scattering)
C. Zeta potential: ELS (Electrophoretic Light Scattering)
D. Can measure granularity distribution and the zeta potential of the particles dispersed in every solvent
E. Can measure the zeta potential on surfaces of flat samples
F. Can control temperature and measure time dependency
G. Can measure a trace amount of a sample
H. Dynamic ranges: sizes from 0.1 nm to 10,000 nm/zeta potential corresponding to 1 nm to 50,000 nm
I. Dynamic range of sample concentration: 0.001 to 40%

Figure 4A:
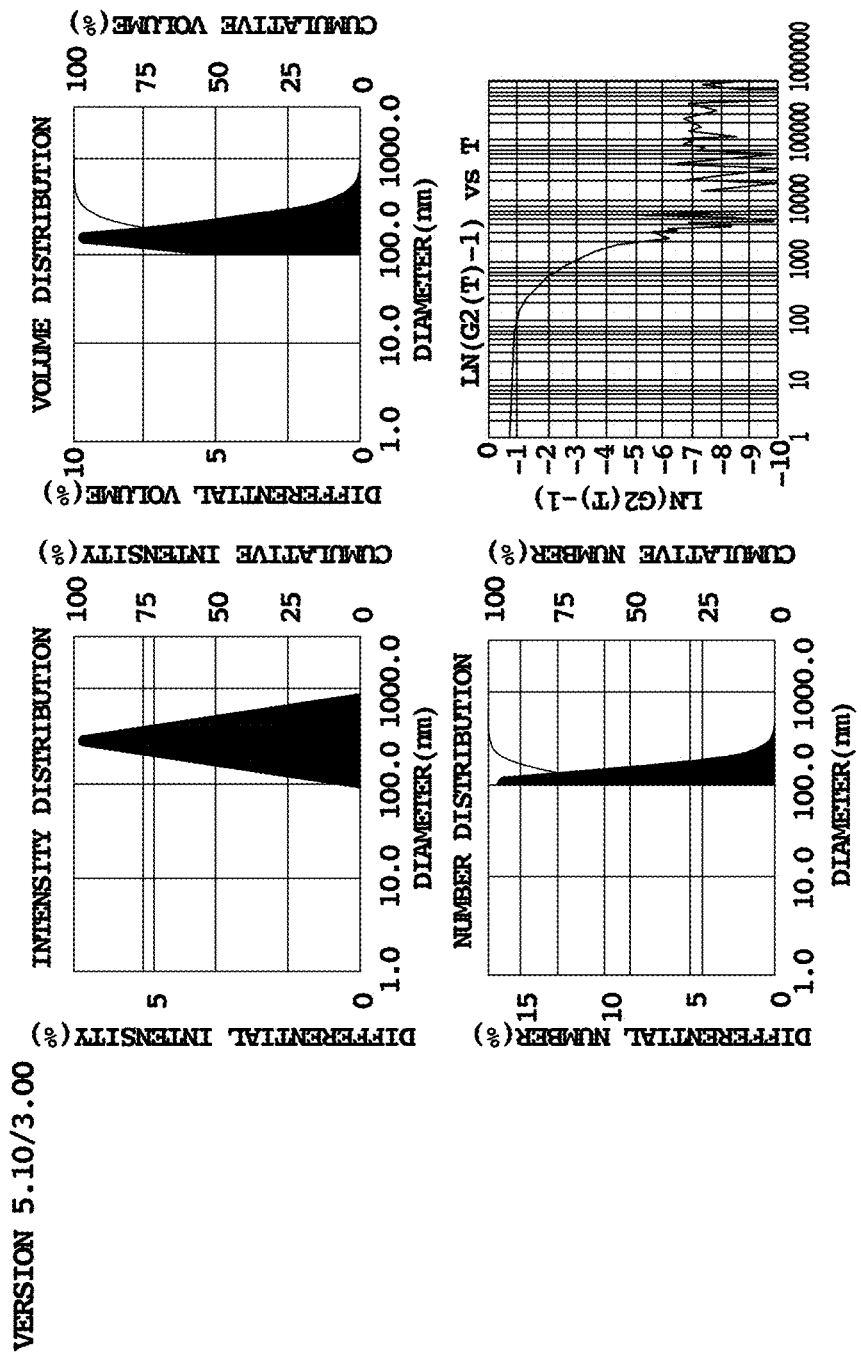

FIGS. 4A to 4B are drawings schematically illustrating results of analyzing the granularity of the microbubbles, where the results show an intensity distribution, a volume distribution, and a number distribution in accordance with one example embodiment of the present disclosure.

Specifically, the results show the intensity distribution of 308 nm, the volume distribution of 184 nm, and the number distribution of 139 nm.

And, FIG. 4C is a drawing schematically illustrating a diameter, a polydispersity index, a dispersion constant, measurement condition, etc. of the microbubbles produced in accordance with the first example embodiment. Herein, the sizes of the microbubbles are measured in environment where the temperature of water is set to 25° C., the viscosity is set to 0.8878 (cP), the scattering intensity is set to 25,762 (cps), and the attenuator is set to 0.72(%).

The microbubbles reactive to the ultrasound produced in accordance with the first example embodiment are measured as having an average diameter of 257.1 nm and the dispersion constant of 1.913e-8 ($cm^2$/sec).

Next, a method of producing the liposomes containing the drugs and the microbubbles 11 whose sizes follow the first uniform distribution is described as follows.

First, solution of source material for the second shells may be prepared.

And second mixture powders including second lipids may be dissolved in organic solvent. Then, the organic solvent may be removed and thus lipid films may be acquired. Herein, the second mixture powders including the second lipids may further include at least one of the albumin, the polymers, and the PEG (polyethylene glycol), and may further include the cholesterol to increase a durability of the liposomes.

Also, the second lipids may include at least one of DPPC(1,2-Dipalmitoyl-sn-glycerol-3-phosphocholine), HSPC(phosphatidylcholine), DDPC(1,2-didecanoyl-sn-glycerol-3-phosphocholine), DEPC(1,2-Di(cis-13-docosenoyl)-sn-glycerol-3-phosphocholine), DOPC(1,2-Dioleoyl-sn-glycerol-3-phosphocholine), DMPC(1,2-Dimyristoyl-sn-glycerol-3-phosphorylcholine), DLPC(1,2-Dilauroyl-sn-glycerol-3-phosphorylcholine), DEPC(1,2-Didecanoyl-sn-glycerol-3-phosphocholine), DSPC(1,2-Distearoyl-sn-glycerol-3-phosphocholine), MPPC(1-myristoyl-2-palmitoyl-sn-glycerol-3-phosphocholine), MSPC(1-myristoyl-2-stearoyl-sn-glycerol-3-phosphocholine), egg PC(phosphocholine), DPPA(Diphenylphosphoryl azide), DMPA-Na(1,2-Dimyristoyl-sn-glycerol-3-phosphate), DPPA-Na(1,2-Dipalmitoyl-sn-glycerol-3-phosphate), DOPA-Na(1,2-Dioleoyl-sn-glycerol-3-phosphate), DSPE (Distearoylphosphatidylethanolamine), DMPE(Dimyristoyl phosphatidylethanolamine), DOPE(Dioleoyl phosphatidylethanolamine), DPPE(Dipalmitoyl phosphatidylethanolamine), DOPE-Glutaryl-(Na)2(1,2-Dioleoyl-sn-glycerol-3-phosphoethanolamine), egg PE(phosphatidylethanolamine), DSPG(Distearoyl phosphatidylglycerol), DMPG-Na(1,2-Dimyristoyl-sn-glycerol-3-Phosphoglycerol), DPPG-Na(1,2-Dipalmitoyl-sn-glycerol-3-Phosphoglycerol), DOPG-Na(1,2-Dioleoyl-sn-glycerol-3-Phosphoglycerol), DOPS (dioleoyl phosphatidylserine), DMPS(Dimyristoyl phosphatidylserine), DMPS-Na(1,2-Dimyristoyl-sn-glycerol-3-phosphoserine), DPPS-Na(1,2-Dipalmitoyl-sn-glycerol-3-phosphoserine), DOPS-Na(1,2-Dioleoyl-sn-glycerol-3-phosphoserine), DSPS (Distearoylphosphatidylserine), DSPE-mPEG(1,2-distearoyl-sn-glycerol-3-phosphoethanolamine-N-[methoxy (polyethylene glycol)-2000]), DSPE-mPEG-2000-Na(1,2-Distearoyl-sn-glycerol-3-phosphoethanolamine), DSPE-mPEG-5000-Na, DSPE-Maleimide PEG-2000-Na, Surfactant: Tween 80, Span 80, dipotassium glycyrrhizinate.

As one example, the liposomes may be comprised of the DPPC (dipalmitoyl-phosphatidyl-choline) and the DPPA (diphenyl-phosphoryl-azide) as the shell material to capture the drugs and genes and to increase a stability of the liposomes. Herein, the DPPC, the DPPA, and the cholesterol may be mixed by a mass ratio of (60% to 85%):(2% to 10%):(10% to 30%). And, the shell material may further include the DSPE-mPEG.

Especially, the DPPA, the DMPA-Na, the DPPA-Na, the DSPG, the DSPS, etc., which are the phospholipids having positive or negative charges, may be selected to allow the liposomes to respectively have net electrical charges.

Also, the albumin may include serum albumin, ovalbumin, etc.

Also, the polymers may include poly(β-benzyl-L-aspartate), PDLA (poly-DL-lactic acid), etc.

Herein, the organic solvent may include solvent of chloroform and methanol which may be mixed by a volume ratio of 1:1 to 3:1.

Also, the second mixture powders may be dissolved in the organic solvent by using a magnetic stirrer at about 40° C. to 60° C. for 10 to 30 minutes.

Also, the organic solvent may be removed through rotary evaporation.

As one example, the organic solvent may be evaporated by using a rotary evaporator at 20° C. to 40° C. for 10 to 30 minutes, and remaining organic solvent may be completely removed through vacuum drying by using a vacuum chamber. Herein, the vacuum drying may be performed preferably for at least 6 hours, and more specifically, 24 hours.

Then, after the chloroform, the methanol, etc. of the organic solvent are evaporated, multiple layers of lipid films may be formed on a bottom of a flask, that is, a film cake of whirled lipid material may be formed on the bottom of the flask.

Next, second solvent of an appropriate amount may be added to the lipid films, for example, PBS (phosphate-buffered saline) may be added for hydration, to thereby produce the solution of the source material for the second shells. And the solution of the source material for the second shells may be deagglomerated by an ultrasound generator. Herein, according to conditions of the drugs and characteristics of the microbubbles 11, the microbubbles 11 whose sizes follow the first uniform distribution and the drugs and/or the genes may be added together and ultrasonically deagglomerated, but the scope of the present disclosure is not limited thereto, and the microbubbles 11 and the drugs and/or the genes may be added after the lipid films are deagglomerated.

Then, the lipid films deagglomerated by the ultrasound generator, the microbubbles 11, and the drugs and/or the genes may result in the liposomes in which the microbubbles 11 and the drugs and/or the genes are included through a self-assembling mechanism.

Figure 5:
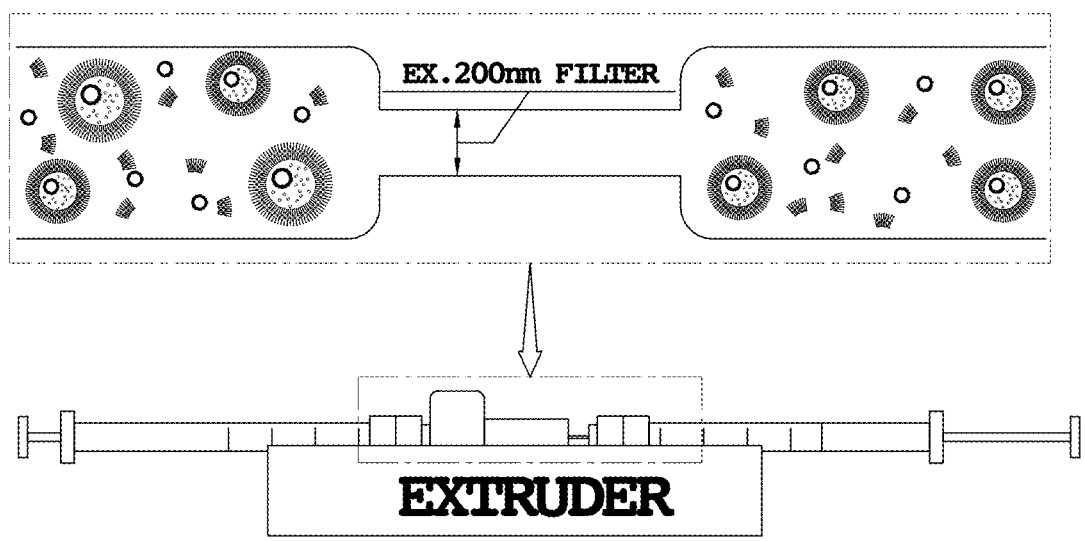
FIG. 5 is a drawing schematically illustrating a process of adjusting sizes of the liposomes in accordance with one example embodiment of the present disclosure.

Next, as shown in FIG. 5, the liposomes with various sizes may be filtered by using the extruder including the second filter, to thereby adjust the sizes of the liposomes. That is, the liposomes with diameters larger than a second pore size of the second filter do not pass pores but are destroyed. And the microbubbles 11, the drugs, the lipid films from the destroyed liposomes may be reassembled. Herein, since the liposomes must be larger than the microbubbles, as shown in FIG. 5 for example, the second filter may have the second pore size of 200 nm, but the scope of the present disclosure is not limited thereto.

Thereafter, a mixture which includes the liposomes whose sizes follow the second uniform distribution through filtering is centrifuged, to thereby precipitate the liposomes. Then the supernatant liquid is removed, and the remainings are washed with the DW (deionized water), and accordingly, the liposomes adjusted to a second desired size may be acquired.

A second example embodiment: producing the liposomes for drug delivery

1. Preparing Shell Material

The DPPC, the DPPA, and the cholesterol are mixed by a mass ratio of 75:5:20, to thereby produce the lipid material. And, the lipid material is dissolved in the organic solvent of the chloroform and the methanol mixed by a volume ratio of 2:1.

And, the organic solvent is evaporated by using a rotating stirrer at 30° C. for 20 minutes.

Then, the remainings are vacuum dried for 24 hours by using the vacuum chamber, to thereby produce the lipid films.

2. Producing the Liposomes

Two milliliters of the PBS is added to the lipid films for hydration, and ultrasonic deagglomeration is performed at room temperature for 1 minute with 100 W of power. Herein, the microbubbles 11 reactive to the ultrasound, prepared as having the sizes following the first uniform distribution in the first example embodiment, and the drugs and/or the genes may be added together. Then, the microbubbles 11 and the drugs and/or the genes may be ultrasonically deagglomerated, to thereby produce the liposomes with various sizes.

3. Adjusting the Sizes of the Liposomes and Reassemblying the Liposomes

The liposomes with the various sizes are filtered by using the extruder including the polycarbonate membrane filter. And the filtered liposomes are centrifuged, to thereby precipitate the liposomes. Then the supernatant liquid is removed and the remainings are washed with the DW (deionized water), and accordingly, the liposomes may be acquired.

4. Analysis by Using the Confocal Microscope

Figure 6:
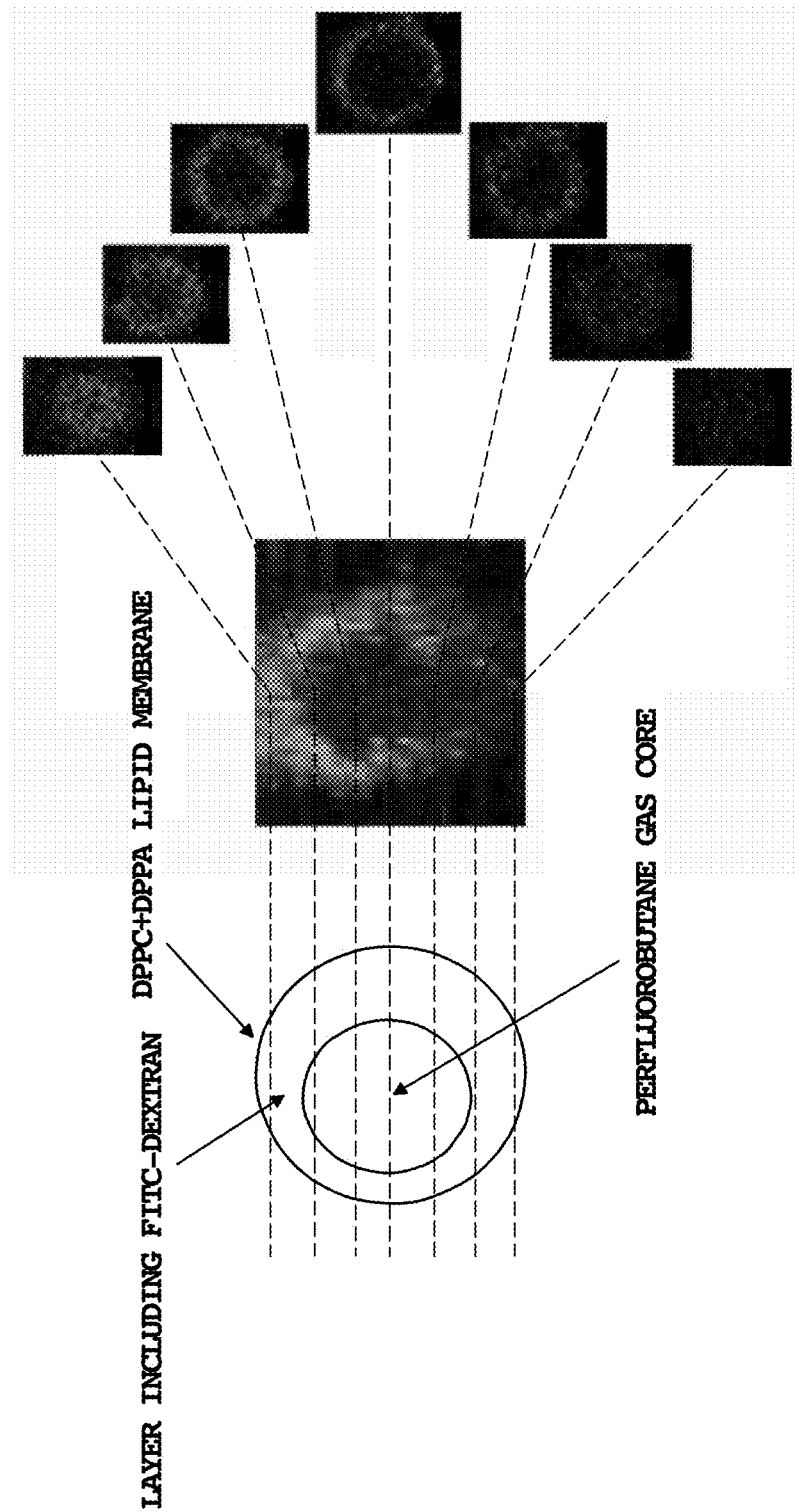
FIG. 6 is a drawing schematically illustrating analysis of the confocal microscope images of the liposomes in accordance with one example embodiment of the present disclosure.

The liposomes capturing the drugs according to the method of the second example embodiment above are observed by using the confocal microscope. And FIG. 6 shows one of the liposomes capturing one of the microbubbles 11, in which a gas core is present, with hydrophilic fluorescence substance (Dextran of MW: 4 k) on outer surfaces of the microbubbles 11.

Figure 7A:
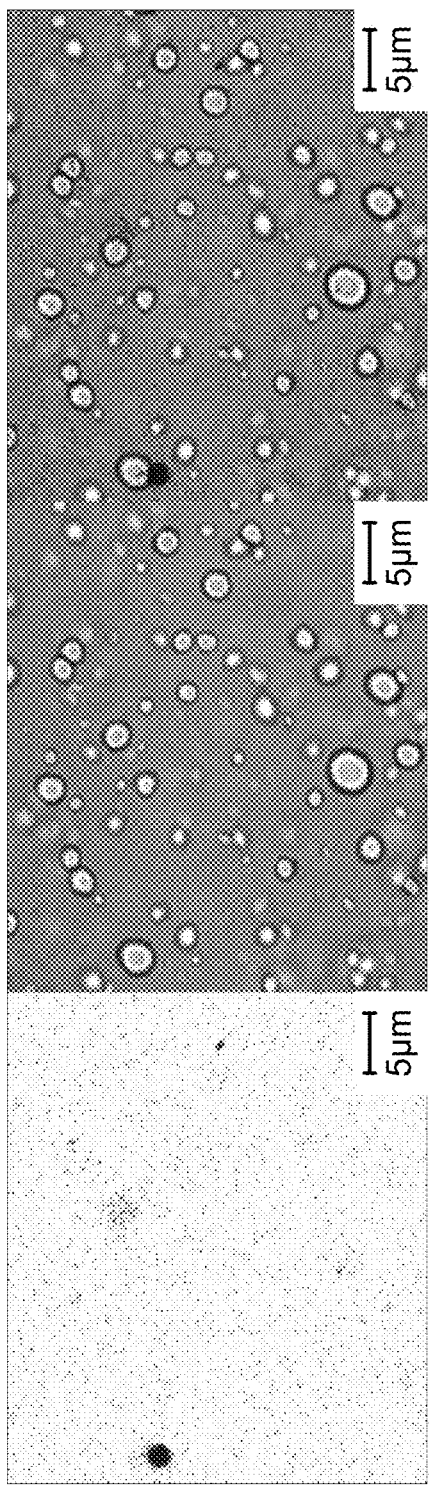
FIG. 7A is a drawing schematically illustrating analyzed confocal microscope images of the liposomes whose sizes are not adjusted according to a conventional technology.
Figure 7B:
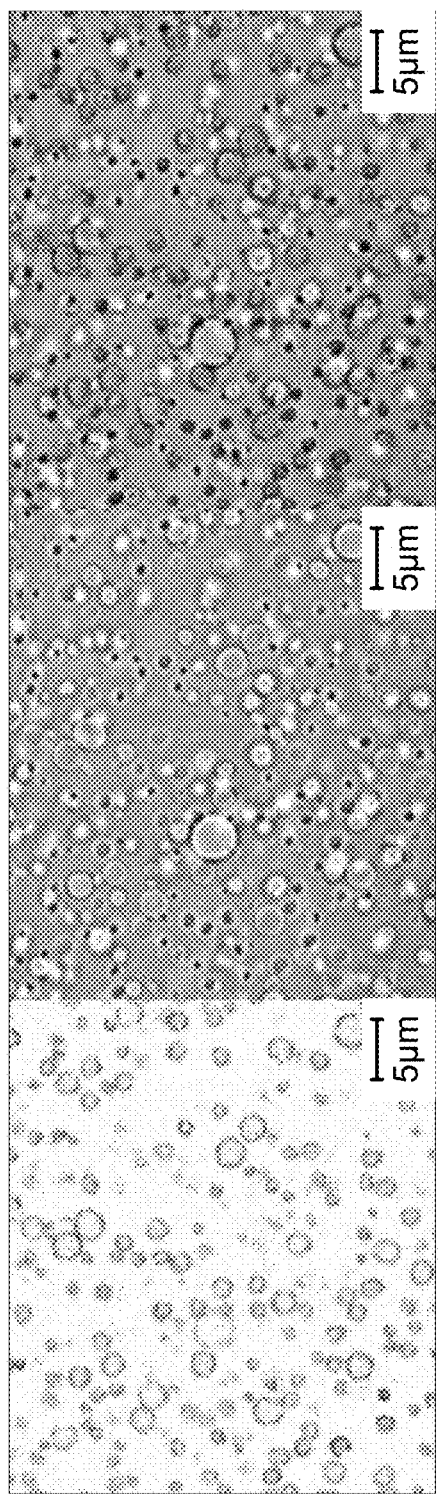
FIG. 7B is a drawing schematically illustrating analyzed confocal microscope images of the liposomes whose sizes are adjusted in accordance with one example embodiment of the present disclosure.

Also, FIG. 7A shows the microbubbles 11 and the liposomes, both of whose sizes are not adjusted. Unlike FIG. 7A, the individual liposomes are shown as capturing the drugs efficiently in FIG. 7B which shows the liposomes produced in accordance with example embodiments of the present disclosure.

5. Experiment of Capturing Gold Nano-Particles

Figure 8:
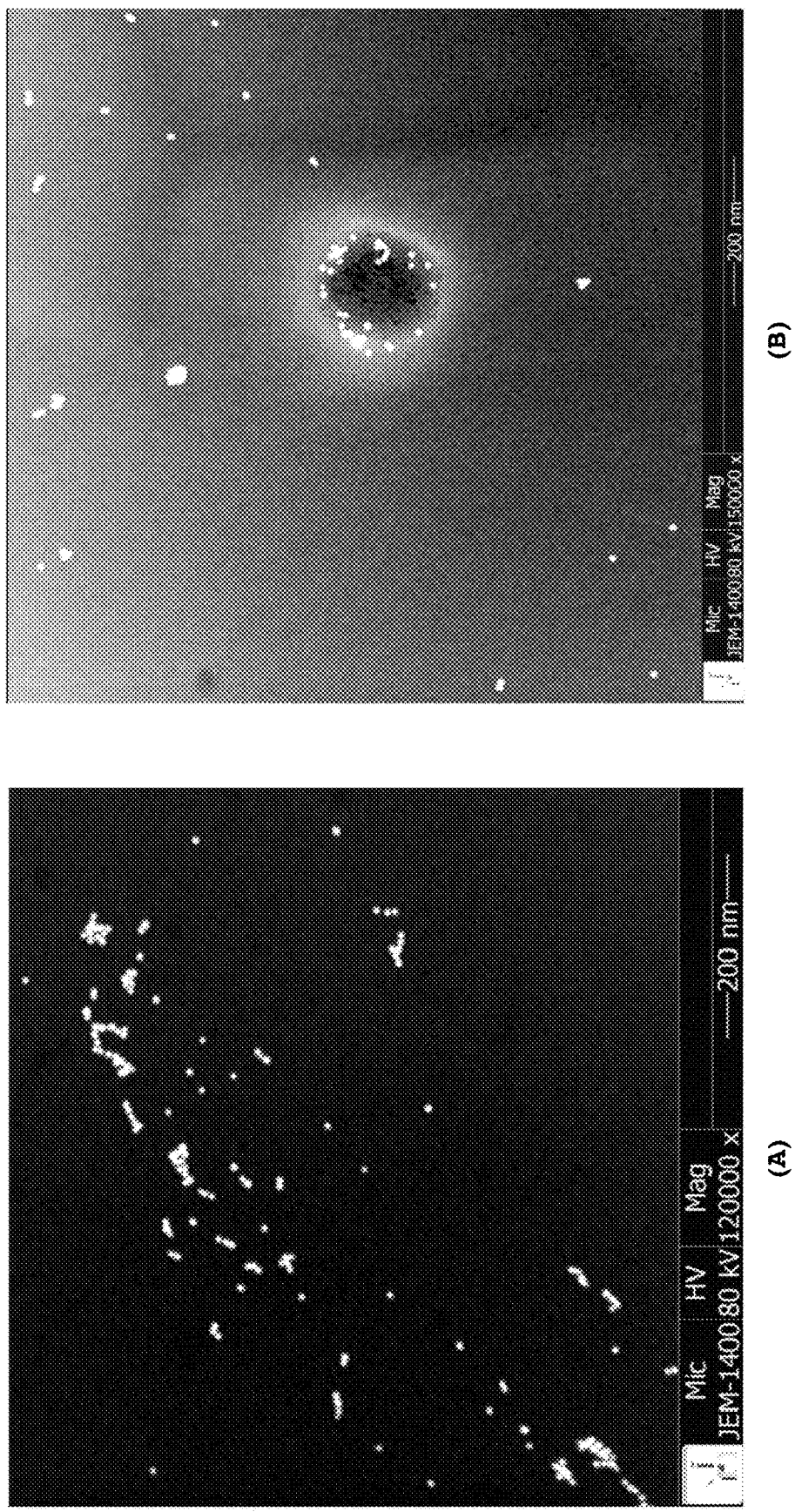
FIG. 8 is a drawing schematically illustrating gold nanoparticles captured by using the liposomes in accordance with one example embodiment of the present disclosure.

In order to analyze the liposomes containing the microbubbles 11 and the hydrophilic drugs by using TEM (transmission electron microscopy) images, the liposomes in accordance with one example embodiment of the present disclosure are placed at a location where the gold nano-particles are present, as shown in (A) of FIG. 8.

And, by referring to the TEM images, the gold nano-particles are trapped in the liposomes containing the drugs and the microbubbles 11 as shown in (B) of FIG. 8, and thus it is confirmed that the drugs in the amount sufficient for an effective dose are loaded into the liposomes.

If the liposomes containing the drugs and the microbubbles 11 prepared as above are irradiated with the ultrasound at a target site, then resulting cavitation effect allows the drugs inside the liposomes to be released at the target site.

Also, targeting ligands such as antibodies and peptides may be combined with outer surfaces of the liposomes containing the drugs and the microbubbles 11 therein in order to improve an efficiency of targeted drug delivery. Herein, the antibodies and the peptides may be prepared as binding to target molecules like proteins on a surface of a specific cell, for example, a cancer cell.

That is, the liposomes for drug delivery in accordance with one example embodiment of the present disclosure may have simultaneous targeting effects of (1) passive target orientation by using focused ultrasound and (2) active target orientation by using specific targeting ligands.

Herein, the targeting ligands such as the antibodies, the proteins, the peptides, receptors, etc. may be determined through ligand library screening against targeted pathogens. And the determined targeting ligands are combined with the outer surfaces of the liposomes. Then, the targeting ligands combined with the outer surfaces of the liposomes may be directed to the targeted pathogens.

The targeting ligands may be combined with the outer surfaces of the liposomes as follows. For example, the liposomes are prepared, where the liposomes are combined with PEG-COOH in accordance with the first and second example embodiments using DNase-free and RNase-free water.

And, EDC(1-ethyl-3-(3-dimethylaminopropyl)-carbodiimide) and N-hydroxysuccinimide are added and stirred at room temperature for 15 minutes, to thereby activate carboxyl groups COOH.

Then, the targeting ligands combined with amino groups NH2 are blended with the liposomes whose N-hydroxysuccinimides are activated, to thereby react the activated carboxyl groups with amines and thus form amides.

The present disclosure has an effect of protecting the drugs from external environment by encapsulating the drugs into the liposomes.

The present disclosure has another effect of preventing drug release into normal tissue and of delivering the drugs only to the target site where ultrasound energy is to be irradiated, taking advantage of a high reactivity to the ultrasound energy.

The present disclosure has still another effect of producing the microbubbles whose sizes follow the first uniform distribution and the liposomes whose sizes follow the second uniform distribution, to thereby quantify an amount of the drugs to be loaded into the liposomes.

The present disclosure has still yet another effect of allowing the drugs to be loaded in the amount sufficient for the effective dose.

As seen above, the present disclosure has been explained by specific matters such as detailed components, limited embodiments, and drawings. They have been provided only to help more general understanding of the present disclosure. It, however, will be understood by those skilled in the art that various changes and modification may be made from the description without departing from the spirit and scope of the disclosure as defined in the following claims.

Accordingly, the spirit of the present disclosure must not be confined to the explained embodiments, and the following patent claims as well as everything including variations equal or equivalent to the patent claims pertain to the category of the spirit of the present disclosure.

What is claimed is:

1. A method for preparing liposomes for drug delivery containing microbubbles reactive to ultrasonic energy, comprising steps of:
   generating the microbubbles including first shells as outer surfaces thereof and including inert gas inside the first shells;
   inserting the generated microbubbles into a first filter with a first size in an extruder, thereby separating a part of the microbubbles with sizes to follow a first uniform distribution through an output port of the first filter;
   generating the liposomes including second shells as outer surfaces thereof and including the separated microbubbles whose sizes follow the first uniform distribution encapsulated within an aqueous interior of the liposomes and drugs; and
   inserting the generated liposomes into a second filter with a second size in the extruder, thereby separating a part of the liposomes with sizes to follow a second uniform distribution through an output port of the second filter.

2. The method of claim 1, further comprising a step of:
   combining targeting ligands with the second shells of the liposomes wherein the targeting ligands react to pathogens at a target site to which the drugs are to be delivered.

3. The method of claim 2, wherein, at the combining step, at least one of one or more antibodies, one or more proteins, one or more peptides, and one or more receptors, each of which reacts to the pathogens, is determined as the targeting ligands through ligand library screening against the pathogens, and wherein the determined targeting ligands are combined with the second shells.

4. The method of claim 2, wherein the targeting ligands are combined with the second shells by:
   introducing carboxyl groups to the second shells;
   activating the carboxyl groups; and
   mixing the targeting ligands with amino groups, the second shells including the activated carboxyl groups, to thereby react the activated carboxyl groups with the amino groups and thus form amides.

5. The method of claim 2, wherein the targeting ligands are combined with the second shells by:
   introducing the carboxyl groups to the second shells;
   adding EDC (1-ethyl-3-(3-dimethylaminopropyl)-carbodiimide) and N-hydroxy succinimide;
   activating the carboxyl groups; and
   mixing the targeting ligands with the amino groups, the second shells including the activated carboxyl groups, to thereby react the activated carboxyl groups with the amino groups and thus form amides.

6. The method of claim 1, wherein the microbubbles are generated by dissolving first mixture powders including first lipids in a first solvent and thus producing a solution of source material for the first shells and mechanically blending the solution of the source material for the first shells with the inert gas.

7. The method of claim 6, wherein the first lipids include at least one of DPPC (1,2-Dipalmitoyl-sn-glycerol-3-phosphocholine), HSPC (phosphatidylcholine), DDPC (1,2-didecanoyl-sn-glycerol-3-phosphocholine), DEPC (1,2-Di (cis-13-docosenoyl)-sn-glycerol-3-phosphocholine), DOPC (1,2-Dioleoyl-sn-glycerol-3-phosphocholine), DMPC (1,2-Dimyristoyl-sn-glycerol-3-phosphorylcholine), DLPC (1,2-Dilauroyl-sn-glycerol-3-phosphorylcholine), DEPC (1,2-Didecanoyl-sn-glycerol-3-phosphocholine), DSPC (1,2-Distearoyl-sn-glycerol-3-phosphocholine), MPPC (1-myristoyl-2-palmitoyl-sn-glycerol-3-phosphocholine), MSPC (1-myristoyl-2-stearoyl-sn-glycerol-3-phosphocholine), egg PC (phosphocholine), DPPA (Diphenylphosphoryl azide), DMPA-Na (1,2-Dimyristoyl-sn-glycerol-3-phosphate), DPPA-Na (1,2-Dipalmitoyl-sn-glycerol-3-phosphate), DOPA-Na (1,2-Dioleoyl-sn-glycerol-3-phosphate), DSPE (Distearoylphosphatidylethanolamine), DMPE (Dimyristoyl phosphatidylethanolamine), DOPE (Dioleoyl phosphatidylethanolamine), DPPE (Dipalmitoyl phosphatidylethanolamine), DOPE-Glutaryl-(Na)2 (1,2-Dioleoyl-sn-glycerol-3-phosphoethanolamine), egg PE (phosphatidylethanolamine), DSPG (Distearoylphosphatidylglycerol), DMPG-Na (1,2-Dimyristoyl-sn-glycerol-3-Phosphoglycerol), DPPG-Na (1,2-Dipalmitoyl-sn-glycerol-3-Phosphoglycerol), DOPG-Na (1,2-Dioleoyl-sn-glycerol-3-Phosphoglycerol), DOPS (dioleoyl phosphatidylserine), DMPS (Dimyristoyl phosphatidylserine), DMPS-Na (1,2-Dimyristoyl-sn-glycerol-3-phosphoserine), DPPS-Na (1,2-Dipalmitoyl-sn-glycerol-3-phosphoserine), DOPS-Na (1,2-Dioleoyl-sn-glycerol-3-phosphoserine), DSPS (Distearoylphosphatidylserine), DSPE-mPEG (1,2-distearoyl-sn-glycerol-3-phosphoethanolamine-N-[methoxy (polyethylene glycol)-2000]), DSPE-mPEG-2000-Na (1,2-Distearoyl-sn-glycerol-3-phosphoethanolamine), DSPE-mPEG-5000-Na, DSPE-Maleimide PEG-2000-Na, polysorbate 80, and dipotassium glycyrrhizinate.

8. The method of claim 7, wherein the first lipids include the DPPC and the DPPA.

9. The method of claim 6, wherein the first mixture powders further include at least one of albumin, one or more polymers, cholesterol, PEG (polyethylene glycol), one or more surfactants, one or more proteins, and one or more biodegradable macromolecules.

10. The method of claim 6, wherein the first solvent includes at least one of saline or triple distilled water, glycerin, and propylene glycol.

11. The method of claim 6, wherein the solution of the source material for the first shells is mixed with the inert gas by a volume ratio of 1:1 to 20:1.

12. The method of claim 1, wherein the first filter has a pore size ranging from 30 nm to 1 µm, to thereby adjust the sizes of the microbubbles to follow the first uniform distribution.

13. The method of claim 1, wherein the inert gas is a perfluorocarbon-based gas.

14. The method of claim 13, wherein the perfluorocarbon-based gas is at least one of perfluoromethane, perfluoroethane, perfluoropropane, perfluorobutane, perfluoro-n-pentane, perfluoro-n-hexane, perfluoromethylcyclopentane, perfluoro-1,3-dimethylcyclohexane, perfluorodecalin, perfluoromethyldecalin, and perfluoroperhydrobenzyltetralin.

15. The method of claim 1, wherein the liposomes are generated by:
dissolving second mixture powders including second lipids in an organic solvent;
removing the organic solvent and thus acquiring lipid films;
dissolving the lipid films in a second solvent and thus producing a solution of source material for the second shells;
mixing the solution of the source material for the second shells with the microbubbles and the drugs; and
irradiating the mixed solution of the source material for the second shells with the ultrasonic energy.

16. The method of claim 15, wherein the second lipids include at least one of DPPC (1,2-Dipalmitoyl-sn-glycerol-3-phosphocholine), HSPC (phosphatidylcholine), DDPC (1,2-didecanoyl-sn-glycerol-3-phosphocholine), DEPC (1,2-Di(cis-13-docosenoyl)-sn-glycerol-3-phosphocholine), DOPC (1,2-Dioleoyl-sn-glycerol-3-phosphocholine), DMPC (1,2-Dimyristoyl-sn-glycerol-3-phosphorylcholine), DLPC (1,2-Dilauroyl-sn-glycerol-3-phosphorylcholine), DEPC (1,2-Didecanoyl-sn-glycerol-3-phosphocholine), DSPC (1,2-Distearoyl-sn-glycerol-3-phosphocholine), MPPC (1-myristoyl-2-palmitoyl-sn-glycerol-3-phosphocholine), MSPC (1-myristoyl-2-stearoyl-sn-glycerol-3-phosphocholine), egg PC (phosphocholine), DPPA (Diphenylphosphoryl azide), DMPA-Na (1,2-Dimyristoyl-sn-glycerol-3-phosphate), DPPA-Na (1,2-Dipalmitoyl-sn-glycerol-3-phosphate), DOPA-Na (1,2-Dioleoyl-sn-glycerol-3-phosphate), DSPE (Distearoylphosphatidylethanolamine), DMPE (Dimyristoyl phosphatidylethanolamine), DOPE (Dioleoyl phosphatidylethanolamine), DPPE (Dipalmitoyl phosphatidylethanolamine), DOPE-Glutaryl-(Na)2 (1,2-Dioleoyl-sn-glycerol-3-phosphoethanolamine), egg PE (phosphatidylethanolamine), DSPG (Distearoylphosphatidylglycerol), DMPG-Na (1,2-Dimyristoyl-sn-glycerol-3-Phosphoglycerol), DPPG-Na (1,2-Dipalmitoyl-sn-glycerol-3-Phosphoglycerol), DOPG-Na (1,2-Dioleoyl-sn-glycerol-3-Phosphoglycerol), DOPS (dioleoyl phosphatidylserine), DMPS (Dimyristoyl phosphatidylserine), DMPS-Na (1,2-Dimyristoyl-sn-glycerol-3-phosphoserine), DPPS-Na (1,2-Dipalmitoyl-sn-glycerol-3-phosphoserine), DOPS-Na (1,2-Dioleoyl-sn-glycerol-3-phosphoserine), DSPS (Distearoylphosphatidylserine), DSPE-mPEG (1,2-distearoyl-sn-glycerol-3-phosphoethanolamine-N-[methoxy (polyethylene glycol)-2000]), DSPE-mPEG-2000-Na (1,2-Distearoyl-sn-glycerol-3-phosphoethanolamine), DSPE-mPEG-5000-Na, DSPE-Maleimide PEG-2000-Na, polysorbate 80, and dipotassium glycyrrhizinate.

17. The method of claim 16, wherein the second lipids include the DPPC and the DPPA.

18. The method of claim 16, wherein the second lipids include at least one of the DPPA, the DMPA-Na, the DPPA-Na, the DSPG and the DSPS, to allow the liposomes to have net electrical charges.

19. The method of claim 15, wherein the second mixture powders further include at least one of albumin, one or more polymers, cholesterol, and PEG (polyethylene glycol).

20. The method of claim 15, wherein the second solvent is PBS (phosphate-buffered saline).

21. The method of claim 15, wherein the organic solvent is a mixture of chloroform and methanol.

22. The method of claim 1, wherein the liposomes are filtered using the second filter to thereby adjust the sizes of the liposomes to follow the second uniform distribution.

23. The method of claim 1, wherein the liposomes are generated by irradiating a solution of source material for the second shells with the ultrasonic energy and then mixing the microbubbles and the drugs with the solution of the source material for the second shells.

24. The method of claim 1, wherein the liposomes further include genes.

* * * * *